United States Patent [19]
Meier

[11] Patent Number: 4,582,922
[45] Date of Patent: Apr. 15, 1986

[54] PROCESS FOR THE PREPARATION OF METHYL N-METHYLANTHRANILATE

[75] Inventor: Eric A. Meier, Hamilton Square, N.J.

[73] Assignee: National Starch and Chemical Corporation, Bridgewater, N.J.

[21] Appl. No.: 697,533

[22] Filed: Feb. 1, 1985

[51] Int. Cl.⁴ .......................................... C07C 101/54
[52] U.S. Cl. .................................................. 560/019
[58] Field of Search ................................... 560/43, 19

[56] References Cited

U.S. PATENT DOCUMENTS 4,255,587  3/1981  Plath et al. ........................... 560/43

OTHER PUBLICATIONS

Wakae et al., Chem. Abs., vol. 49 (1955) 955a.
J. Soc. Org. Synthetic Chem. (Japan) Chem. Abst. 49 955a (1955), "Synthesis of Alkylanthranilic Acid by Reductive Alkylation."
Aust. J. Chem. 27 537–542 (1974), "Synthesis of an Arylhydroxytetronimide and 3-Hydroxy-4 (1H)-Quinolone Derivatives."
J. Org. Chem. 24 1214 (1959) "Isatoic Anhydride IV. Reactions with Various Nucleophiles."

*Primary Examiner*—Bernard Helfin
*Attorney, Agent, or Firm*—Edwin M. Szala; Ellen T. Dec

[57] ABSTRACT

A mixture of methyl anthranilate, dissolved in a water-miscible solvent, with a solution of formaldehyde is reduced in a hydrogen atmosphere in the presence of a hyrogenation catalyst at moderate temperatures and pressures to yield methyl N-methylanthranilate. The invention provides a process which is feasible towards producing the compound in commercial quantities in high purity and good yield.

8 Claims, No Drawings

PROCESS FOR THE PREPARATION OF METHYL N-METHYLANTHRANILATE

BACKGROUND OF THE INVENTION

The present invention relates to the field of organic chemistry and more specifically to the preparation of methyl N-methylanthranilate.

At least two processes for the preparation of the subject compound are known in the prior art. In one such process anthranilic acid is used as the starting compound and reacted with formaldehyde and hydrogen as described in J. Soc. Org. Synthetic Chem. (Japan) 11,434 (1953), Chem. Abst. 49, 955a (1955), to produce N-methylanthranilic acid. This resulting intermediate is thereafter reacted with thionyl chloride and methanol to produce the desired methyl N-methylanthranilate. This step is described in Aust. J. Chem. 27, 537 (1974). The disadvantages of this process lie in the use of a relatively expensive starting material and the relatively poor yields of final product. Typical reported reaction yields based on the starting compound amount to about 36% overall for the two steps.

In another prior art process, described in J. Org. Chem. 24,1214 (1959), the starting compound is N-methylisatoic anhydride, again a costly starting material which is more expensive than anthranilic acid.

Methyl N-methylanthranilate has found use in the preparation of artificial food flavorings. The compound has been disclosed to be offensive to birds and has "very excellent repellent action for prolonged periods in very small concentrations" according to U.S. Pat. No. 2,967,128 which issued on Jan. 3, 1961.

It is an object of this invention to provide a process for the preparation of methyl N-methylanthranilate which is feasible towards producing the compound in commercial quantities, in high purity and good yield.

SUMMARY OF THE INVENTION

The present application discloses a process for the preparation of methyl N-methylanthranilate (DMA) comprising the use as starting material of methyl anthranilate. In accordance with the invention, the process involves forming a mixture of methyl anthranilate dissolved in a water-miscible solvent such as, for example, isopropanol or methanol, with an aqueous or alcoholic solution of formaldehyde. The resulting honogeneous mixture (solution) is reduced in a hydrogen atmosphere in the presence of a hydrogenation catalyst at moderate temperatures and pressures. The resultant product is recovered from the reaction mixture by fractional vacuum distillation.

The process may be illustrated by the following equation:

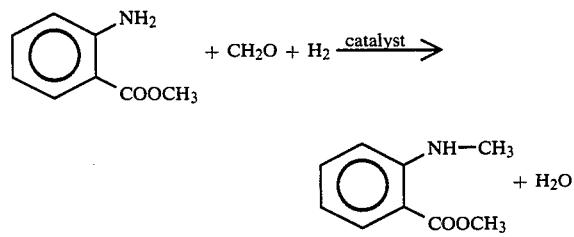

The reductive methylation produces water as a by-product. The feature of the process lies in the reductive methylation of the amino group in the presence of what is normally considered to be a water-sensitive hydrolyzable ester group which unexpectedly survives the methylation conditions.

DETAILED DESCRIPTION OF THE PREFERRED EMBODIMENTS

The preparation of the methyl N-methylanthranilate in accordance with the invention is carried out employing a process involving reactive methylation.

The preparation is started by first providing a mixture of methyl anthranilate and formaldehyde in a suitable pressure reactor, i.e. a vessel which is able to withstand superatmospheric pressures. To provide a fluid medium for reaction, the methyl anthranilate is generally dissolved in water-miscible solvent such as a lower alkanol. Suitable water-miscible solvents include alkanols, cyclic and acyclic ethers and mixtures thereof. Typical useful solvents include methanol, isopropanol and p-dioxane. Isopropanol and methanol are preferred solvents with isopropanol being most preferred. Use of methanol leads to a twophase system during the recovery of the product while use of isopropanol maintains a one-phase system. The proportion of starting compound to solvent is not critical and can vary over a wide range, but a preferable proportion is from about 1:1 to 1:8, and most preferable is from about 1:2 to 1:4.

The formaldehyde needed in the reaction mixture is used as an aqueous or alcoholic solution. Most conveniently, it is used as a 37% aqueous solution or 55% methanolic solution, both as commercially supplied. The methyl anthranilate and formaldehyde are used on a mole to mole ratio but a slight excess (up to about 10 mole percent) of either reactant is permissible. An equimolar ratio is preferred.

The catalyst useful in carrying out the reducing reaction is not critical and may be any of the common hydrogenation catalysts known in the art. Most useful, however, are Raney nickel and noble metal catalysts such as palladium on charcoal. As is known, palladium on charcoal permits the hydrogenation to proceed at lower operating pressures than Raney nickel. The catalyst is added to the reaction mixture in amounts known in the art of hydrogenation. Ordinarily, the amounts used in the present reaction will range from about 1 to 10% by weight based on the participating reactants.

In carrying out a reaction according to the present invention, the reaction vessel head space and the reaction mixture of methyl anthranilate, formaldehyde and catalyst are purged with hydrogen to be free of air, and the mixture is gently heated to about 30° to 40° C. The system is pressurized with additional hydrogen to a pressure of about 150 to 1,000 pounds per square inch (psi). Typical operating pressures will be in the range of 150 to 750 psi depending on the desired reaction rates and the specific catalyst employed. Moderate heating is continued to reach an operating temperature of about 35° to 75° C. Preferred temperatures will be in the range of about 35°-55° C. The reaction is allowed to proceed with periodic repressurization as necesssary until no further decrease in hydrogen pressure (due to reaction) is observed, usually a period of from about 2-12 hours, preferably about 2-8 hours.

When the reaction is completed, the vessel is cooled to room temperature and the reaction mixture is filtered to remove the catalyst. The bulk of the solvent is removed by vacuum distillation, usually at pressures of about 100-300 mm Hg. and temperatures of 25°-90° C.

Depending on the solvent used in the reaction mixture, phase separation may or may not occur. Where phase separation occurs, the aqueous (non-product) phase is decanted. The remaining phase contains the product and is subjected to vacuum distillation to recover the product as a colorless liquid having a boiling point in the range of 138°-143° C. at 21 mm Hg. or 104°-108° C. at 0.5 mm Hg. As is known, the boiling point range is dependent on the specific vacuum applied to the system.

Where phase separation does not occur after stripping, the product is further purified by direct vacuum distillation.

This invention is further illustrated in connection with the following examples. In these examples, all parts are given by weight unless otherwise noted.

EXAMPLE I

Preparation of Methyl N-Methylanthranilate

A two liter high pressure reactor equipped with a mechancial stirrer is charged with the following:
a. Methyl anthranilate—226.8 grams (1.50 moles)
b. Methanol—1270. ml
c. Aqueous formaldehyde (37%)—121.6 grams (1.50 moles)
d. Raney nickel (W-2 grade)—13.2 grams The mixture is stirred to achieve a homogeneous slurry. The slurry and head space are purged free of air using hydrogen, and the system is heated to 36° C. The system is then pressurized to about 600 psi and allowed to consume hydrogen while gradual heating is applied. The hydrogenation is allowed to proceed in the 36°-72° C. range with repressurization to 700 psi until no further hydrogen is consumed in the reaction, about 2 hours. The reactor is cooled to room temperature and the catalyst is removed by filtration. The bulk of the solvent is stripped off while raising the temperature to 90° C. at 40 mm Hg. vacuum resulting in a layering of the product.

The two-phase system is treated with 600 ml of toluene and 300 ml of water with mechanical agitation at room temperature. The aqueous phase is decanted and the toluene layer vacuum distilled using a six-inch Vigereaux column collecting the fraction boiling at 138°-143° C. at 21 mm Hg. The yield is 171 grams of 98.7% pure methyl N-methylanthranilate which calculates to be 69% of theory.

EXAMPLE II

The procedure of Example I was repeated substantially as described with slight variations as noted to obtain seven additional preparations of the subject compound.

| Batch No. | Solvent | Formaldehyde | Reaction Period | Distilled Yield | Purity |
|---|---|---|---|---|---|
| 4707-64BB | MeOH | Aqueous (37%) | 5.0 hours | 69.0% | 97.1% |
| 4707-79B | MeOH | Aqueous (37%) | 4.0 hours | 86.6% | 93.8% |
| 4707-82 | i-PrOH | Aqueous (37%) | 3.5 hours | 97.0%* | 88.7% |
| 4707-133 | i-PrOH | Alcoholic (55%) | 3.0 hours | 92.0% | 92.0% |
| 4707-86B | i-PrOH | Aqueous (37%)** | <8.0 | 91.6% | — |
| 4707-89B | i-PrOH | Aqueous (37%)** | 5.0 hours | 74.5% | — |
| 4707-91B | MeOH | Aqueous (37%)** | <8.0 hours | 91.4% | 94.3% |

*undistilled
**10 mole percent excess

EXAMPLE III

In a manner similar to the procedure of Example I, a preparation of the subject compound was made employing palladium on charcoal (5% by weight based on reactants) as the hydrogenation catalyst. Alcoholic formaldehyde was used. The system was pressurized to about 150 psi and the reaction was allowed to proceed in a temperature range of 38°-50° C. The reaction was terminated prior to completion resulting in a yield of methyl N-methylanthranilate of 13% of theory.

In summary the invention provides a process for the preparation of methyl N-methylanthranilate employing methyl anthranilate as the starting material, which process yields the compound in high purity and good yield.

Now that the preferred embodiments of the present invention have been described in detail, various modifications and improvements thereon will become readily apparent to those skilled in the art. Accordingly, the spirit and scope of the invention are to be limited only by the following claims and not by the foregoing specification.

What is claimed is:
1. A process for the preparation of methyl N-methylanthranilate comprising the steps of:
    (a) forming a reaction mixture of methylanthranilate dissolved in a water-miscible solvent with a solution of formaldehyde, wherein the methylanthranilate and formaldehyde are employed in an equimolar ratio or the methylanthranilate or formaldehyde is present in an excess of up to about 10 mole percent, and
    (b) reducing the reaction mixture in a hydrogen atmosphere in the presence of a hydrogenation catalyst at temperatures of about 35°-75° C. and pressures of about 150 to 1,000 pounds per square inch to yield the methyl N-methylanthranilate.
2. The process of claim 1 wherein the hydrogenation catalyst is selected from the group of Raney nickel and palladium on charcoal.
3. The process of claim 1 wherein the water-miscible solvent is selected from the group consisting of methanol and isopropanol.
4. The process of claim 1 wherein the solution of formaldehyde is aqueous solution.
5. The process of claim 1 wherein the solution of formaldehyde is an alcoholic solution.
6. The process of claim 1 wherein the resultant product from the reaction mixture is recovered by vacuum distillation.
7. The process of claim 1 wherein the mixture of step (a) is reduced for a period of from about 2-12 hours.
8. The process of claim 1 wherein the resultant product is recovered by vacuum distillation collecting the fraction having a b.p. range of 138°-143° C. at 21 mm of Hg. or 104°-108° C. at 0.5 mm of Hg. or comparable temperature and pressure.

* * * * *